United States Patent [19]

Meyers

[11] Patent Number: 4,767,718

[45] Date of Patent: Aug. 30, 1988

[54] FLUORESCENT OPIOID REAGENTS AND METHODS OF USE THEREOF IN THE DETECTION OF OPIOID RECEPTORS

[75] Inventor: Vera K. Meyers, Carbondale, Ill.

[73] Assignee: Southern Illinois University Foundation, Carbondale, Ill.

[21] Appl. No.: 621,384

[22] Filed: Jun. 18, 1984

[51] Int. Cl.$^4$ ............................................. G01N 33/94
[52] U.S. Cl. ................................... 436/501; 436/503; 436/800; 436/815; 436/816; 435/4; 435/29; 424/3; 424/7.1; 546/44; 546/45; 546/46; 546/74; 546/97; 546/107
[58] Field of Search ...................... 546/44, 45, 46, 74, 546/97, 107; 436/501, 503, 504, 518, 815, 816, 800; 435/4, 29; 424/3, 7.1

[56] References Cited

U.S. PATENT DOCUMENTS 4,213,904  7/1980  Haugland ............................ 544/212
4,608,376  8/1986  Pasternak ............................ 514/282

OTHER PUBLICATIONS

Blanchard, Methods in Enzymology, vol. 103, pp. 219-227; Academic Press, 1983.
Schiller, Biochemistry 16(9), pp. 1831-1838, 1977.
Kolb: Chemical Abstracts 100:61308m (1983).
Koman: Chemical Abstrcts 103:19359r (1984).

Primary Examiner—Sidney Marantz
Assistant Examiner—Robert Benson
Attorney, Agent, or Firm—Senniger, Powers, Leavitt and Roedel

[57] ABSTRACT

Fluorescent reagents useful as opioid receptor probes. Opioids labeled at the 3 position with fluorescers are useful in various in vivo and in vitro methods for the detection and quantification of receptor sites in tissue cells and subcellular particles.

36 Claims, 1 Drawing Sheet

FLUORESCENT OPIOID REAGENTS AND METHODS OF USE THEREOF IN THE DETECTION OF OPIOID RECEPTORS

BACKGROUND OF THE INVENTION

This invention relates to the field of detection of opioid receptor sites in normal and abnormal tissue cells and subcellular particles and, more particularly, to novel methods for detection and quantification of opioid receptors in such substrates, and novel fluorescent non-peptide opioid agonists and antagonists useful in such methods.

In the study of various neurological disorders, addictions, tolerances, and other pathological conditions of the brain, efforts have been made to develop correlations between such conditions and the histochemical characteristics of brain tissue containing opioid receptor sites. Most of what is known about opioid/receptor interaction has evolved from studies using radiolabeled lignds. These have proved useful for studies at the level of whole animals, organs, tissues, single cells and subcellular fractions.

Fournie-Zaluski et al., Biochem. Biophys. Res. Comm., Vol. 83, pp. 300–305 (1978), and Hazum et al., Science, Vol. 206, pp. 1077–1079 (1979), describe fluorescent enkephalin derivatives having biological activity. These fluorescent peptide reagents have been used for a fluorometric study of the degradation of enkephalins by aminopeptidases from mouse striatum, Guyon et al., Biochem. Biophys. Res. Comm., Vol. 88, pp. 919–926 (1979), and for the study of opioid clustering of enkephalin receptors in neuroblastoma cells, Hazum et al. supra, and Hazum et al., Nature, Vol. 282, pp. 626–628 (1979). Attempts have also been made in the art to develop fluorescent labeled non-peptide opioids. For example, Ullman U.S. Pat. No. 4,160,016 describes a competitive binding assay for determining various ligands by incubating with a ligand analog-fluorescer and an anti-ligand which binds with both the unknown and the ligand analog. Ullman U.S. Pat. No. 4,161,515 uses the same type of ligand analog-fluorescer in a competitive binding assay for the determination of anti-ligand. Among the ligand analog-fluorescers disclosed by Ullman are morphine and morphine derivatives having a fluorescer bound to the 3 position of the opioid.

Correa et al. "Fluorescent Probes of α and β Adrenergic and Opiate Receptors: Biochemical and Histochemical Evaluation" Neurosci. Lett., Vol. 16, pp. 47–53 (1980), describe a fluorescent derivative of naloxone prepared by condensing a dansyl derivative at the 6-position of naloxazone. This fluorescent reagent was tested as a potential in vivo fluorescent label for opioid receptors but was found not to be practical since lipofuscin, which is endogenous to the brain tissue, exhibited autofluorescence at the same frequencies at which fluorescent emissions were obtainable from the dansyl moiety. However, by radiolabeling it was determined that the dansyl substituted nalaxozone had an affinity for opioid receptor sites, a result which the authors deemed surprising in view of the relatively large size of the dansyl moiety.

SUMMARY OF THE INVENTION

Among the several objects of the present invention may be noted the provision of a novel method for detecting the presence of opioid receptors in a sample of tissue, cells or subcellular particles; the provision of such a method which provides for quantification of opioid receptor sites; the provision of a method for determining the distribution of a particular type of opioid receptor site in a tissue sample; the provision of a method for detecting a neurological disorder, addiction, tolerance or pathological condition of a patient by in vitro analysis of a tissue sample taken from an organ of a patient; the provision of a method for in vivo detection of a neurological disorder, addiction, tolerance or other pathological condition in a patient; the provision of novel fluorescent reagents useful as receptor probes in the aforesaid methods; and the provision of processes for the preparation of such fluorescent reagents.

Briefly, therefore, the present invention is directed to a fluorescent agent useful as a receptor probe in the detection and quantification of tissue, cells, and subcellular particles containing opioid receptors. The reagent corresponds to the formula

or

where Fl comprises a fluorescent moiety that emits visible light at a frequency different from any frequency at which light is emitted by any fluorescent moiety endogenous to human brain tissue, and R comprises a non-peptide opioid moiety.

The invention is also directed to a fluorescent reagent having the aforesaid utility and corresponding to the formula

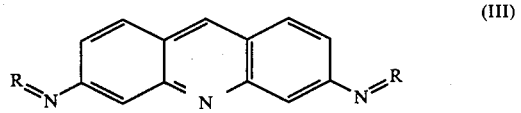

where R comprises a non-peptide opioid moiety.

The invention is further directed to a novel method for the detection of opioid receptor sites in a sample of tissue, cells or subcellular particles. In accordance with the method, the sample is contacted with a fluorescent reagent of the above noted type, unbound reagent is removed from the sample, and the sample thereafter observed for fluorescent staining, such staining being indicative of binding of the reagent to opioid receptor sites in the sample.

The invention is additionally directed to a method for determining the distribution of a particular type of opioid receptor sites in a tissue sample. In this method, the sample is contacted with a receptor probe reagent of one of the aforesaid types, and the fluorescent staining pattern exhibited by the sample is observed, thereby providing an indication of said distribution.

Further encompassed by the invention is a method for detecting a neurological disorder, addiction, tolerance or pathological condition of a patient by in vitro analysis of a tissue sample taken from an organ of the patient. In this method, the sample is contacted with receptor probe reagent of the above type. The fluorescent staining pattern exhibited by the sample is then observed and compared with the staining pattern obtained upon contacting a standard tissue specimen with the reagent, the standard specimen having a staining pattern associated with a known neurological disorder, addiction, tolerance or other pathological condition.

This invention is also directed to a method for in vivo detection of a neurological disorder, addiction, tolerance or other pathological condition of a patient. In this method, a radiolabeled fluorescent reagent of the above type is injected into the patient and observation is made of the radioactive emission pattern obtained after a quantity of the reagent has become bound to receptor sites of the organ. That emission pattern is compared with a standard binding pattern of the fluorescent reagent that is associated with a known neurological disorder, addiction, tolerance or other pathological condition.

The invention is further directed to a process for preparing a fluorescent non-peptide opioid compound corresponding to formula

  (I)

where Fl is a fluorescent moiety that emits visible light at a frequency different from any frequency at which light is emitted by any fluorescent component endogenous to human brain tissue, and R is a non-peptide opioid moiety corresponding to the formula

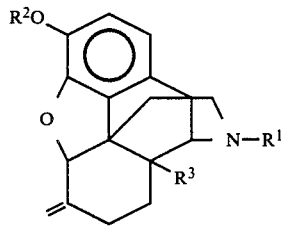  (II)

where $R^1$ is selected from the group consisting of hydrogen, alkyl, alkenyl, and alicyclic, $R^2$ is selected from the group consisting of hydrogen, alkyl, and acyl, and $R^3$ is selected from a group consisting of hydrogen, hydroxyl, and acyloxy. The process comprises reacting an isothiocyanate compound corresponding to the formula

  (IV)

where Fl is as defined as above, with a non-peptide opioid hydrazone compound corresponding to formula

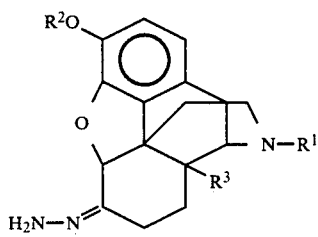  (V)

where $R^1$, $R^2$ and $R^3$ are defined as above.

Also included in the invention is a process for the preparation of a fluorescent non-peptide opioid compound corresponding to the formula:

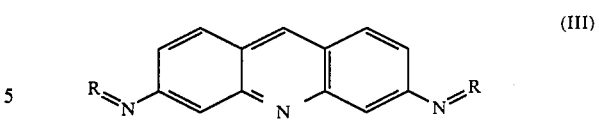  (III)

where R is as defined above. In this process, a compound selected from the group consisting of 3,6-diaminoacridine and hydrohalides thereof is reacted with a non-peptide opioid compound corresponding to the formula

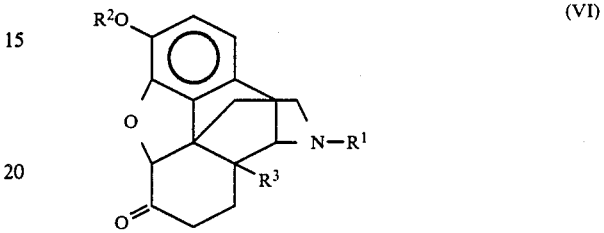  (VI)

where $R^1$, $R^2$ and $R^3$ are as defined above.

Other objects and features will be in part apparent and in part pointed out hereinafter.

DESCRIPTION OF THE PREFERRED EMBODIMENTS

Figure 1:
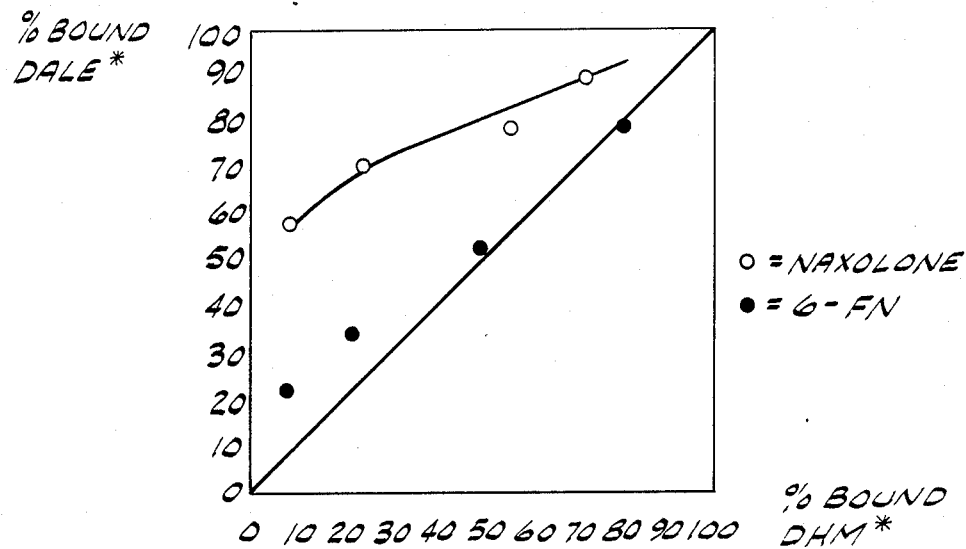
FIG. 1 is a plot comparing the extent of displacement of two different radiolabeled indicator ligands in opioid receptor site selectivity tests conducted on 1-(N)-fluoresceinyl naloxone thiosemicarbazone ("6-FN")

In accordance with the present invention, novel fluorescent reagents have been discovered in which non-peptide opioids are labeled with fluorescers that emit visible light at frequencies different from any frequency at which light is emitted by any endogenous component of human brain tissue. It has further been found that these fluorescent reagents retain the biological activity of the opioids. More particularly, useful biological activity has been found in fluorescent reagents obtained by attaching a fluorescent moiety via a thiosemicarbazone or azine linkage to the 6-position of an opioid moiety having a morphinan or benzomorphan type structure.

Although the activity of the fluorescent labeled opioid is typically decreased, for example, by an order of magnitude, as compared to the unlabeled opioid, the activity of the fluorescent reagent remains sufficient for highly useful application in the detection and quantification of opioid receptor sites in samples of tissue, cells, and subcellular particles. Thus, novel methods have been discovered which utilize the fluorescent reagent as a receptor probe in determining the distribution of receptor sites in a sample of tissue. It has further been found that the fluorescent reagent can be used in novel methods for detecting a neurological disorder, addiction, tolerance or other pathological condition of a patient, either by in vitro analysis of a tissue sample taken from an organ of a patient or by injection of a radiolabeled fluorescent reagent into the patient. In the latter instance, standard binding patterns as compared with the emission pattern obtained after the fluorescent reagent has become bound to receptor sites in the patient's body.

A preferred fluorescent reagent corresponds to the formula

(I)

where Fl comprises a fluorescent moiety that emits visible light at a frequency different from any frequency at which light is emitted by any fluorescent moiety endogenous to human brain tissue, and R is a non-peptide opioid moiety. Alternatively, the linking group may be azino (diazanetetrayl) rather than thiosemicarbazone, i.e., the reagent corresponds to the formula

 (IA)

where Fl and R are as defined above.

The thiosemicarbazone linkage is preferred because of both its stability in vivo and its resistance to cleavage under the influence of enzymes that may be present in tissue samples subjected to in vitro analyses.

Preferably, R has either a morphinan, morphine (4,5 expoxymorphinan) or benzomorphan type structure. In the context of this disclosure, a morphinan type structure is the four ring structure characteristic of those compounds of which morphinan is considered in the art to be the "parent," while a "morphine" type structure is the five ring structure of which 4,5 epoxymorphinan is considered the parent. As used herein, these generic terms specifically include both 7,8-dihydro and 7,8-unsaturated structures. Thus, R includes moieties derived from such common opioids as morphine, codiene, thebaine, oxymorphone, oxycodone, naloxone, naltrexone and the like. Similarly, in this disclosure a benzomorphan type structure is one having the characteristic three ring structure of which benzomorphan is recognized in the art as the parent compound.

R can be derived from an opioid agonist, an opioid antagonist, or an opioid of mixed agonist and antagonist properties. In the structures of Formulae I, Ia and III, R imparts to the fluorescent reagent properties which are similar to, though generally of lesser strength than, the opioid from which R is derived. For use in the methods of the invention, as described below, it is preferred that R be derived from an antagonist rather than an agonist. By nature antagonists have superior binding properties, which enhance the effectiveness of the reagent as a receptor site probe. Also, in the case of in vivo application, the neurological/systemic side effects are less where R is an antagonist.

For most applications it is preferred that R be a morphinan type, more preferably corresponding to the formula

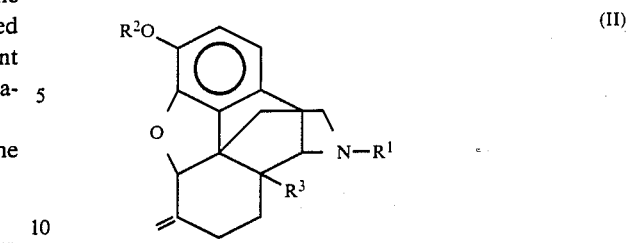

(II)

where $R^1$ is hydrogen, alkyl, alkenyl, or alicyclic, $R^2$ is hydrogen, alkyl, or acyl and $R^3$ is hydrogen, hydroxyl, or acyloxy. Among the various groups which may typically comprise $R^1$ are methyl, ethyl, propyl, cyclopropylmethyl and allyl (2-propenyl).

A variety of fluorescers (fluorescent moieties) can constitute Fl in Formulae I and IA, but this portion of the reagent molecule should not emit visible light at a frequency at which light is emitted by a component endogenous to human brain tissue, such as lipofuscin. Thus, fluorescers such as the dansyl moiety should be avoided. Surprisingly, however, it has been discovered that biological activity is retained and the problem of background autofluorescence avoided by using fluorescers having molecular weights even higher than the dansyl moiety. Particularly preferred fluorescers include substituted and unsubstituted fluoresceinyl, and substituted and unsubstituted rhodaminyl. Especially preferred are fluoresceinyl and tetramethylrhodaminyl-B-. Where the linkage comprises azino (Formula IA) the fluorescer may advantageously be a residue of G-orange or acridone, for example.

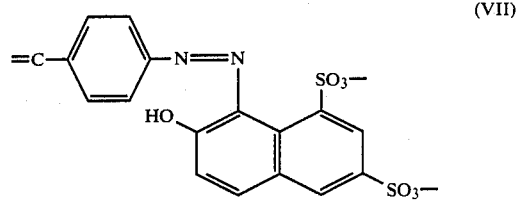

(VII)

or

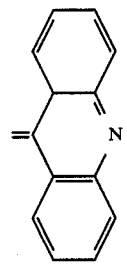

(VIII)

At least in part because of the presence of the azine linkages, these reagents are believed to be particularly persistent in their binding properties. They may, therefore, be particularly useful in applications where long-term staining of cells or tissue is necessary.

In the instance where the linkage comprises a thiosemicarbazone, the fluorescent reagent of Formula I is preferably prepared by a novel process in which an isothiocyanate compound corresponding to the formula

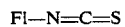 (IV)

is reacted with a non-peptide opioid hydrazone compound corresponding to the formula

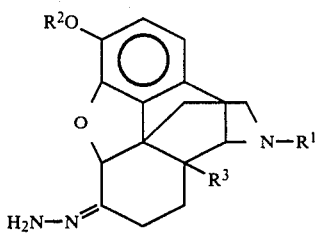

where $R^1$, $R^2$, and $R^3$ are as defined above. Preferably the process is carried out in a liquid medium comprising a solvent for both the isothiocyanate and opioid hydrazone compounds. In order to promote the nucleophilic reaction and facilitate separation after the reaction is complete, the liquid reaction medium also preferably contains a non-solvent for the product fluorescent opioid; for example, a primary alcohol such as methanol, ethanol, propanol, or n-butanol. A preferred solvent component of the reaction system is tetrahydrofuran.

Reaction is conveniently carried out at room temperature using substantially stoichiometrically equivalent proportions of reactants. In order to avoid interference with the binding capacity of the fluorescent reagent, the presence of residual opioids should be minimized, so that a slight excess of fluorescent compound isothiocyanate is preferred. Although the sequence of addition is not critical, the opioid 6-hydrazone is preferably added to the fluorescent compound isothiocyanate since the hydrazone may rearrange to an azine if present in excess in the reaction of the mixture. The product fluorescent reagent is preferably recovered from the reaction mixture by crystallization. This may be initiated by addition of further quantities of non-solvent to the reaction mixture. This results in precipitation of the fluorescent reagent product, while any unreacted opioid is taken up in the alcohol. Several crops of product crystals can be obtained by progressively adding further amounts of non-solvent, for example mixtures of a primary alcohol and water.

Although the opioid hydrazone substrate used in this synthesis may typically be a mixture of syn and anti-stereoisomers, the product fluorescent labeled opioids essentially exclusively anti-isomer.

In an alternative embodiment of the invention, the fluorescent reagent comprises an acridine fluorescer having two opioid moieties attached thereto through Schiff's base —C=N— linkages:

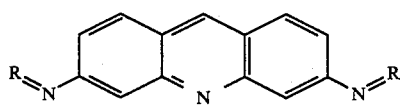

where R is defined as above. This reagent may be particularly advantageous in application of fluorescent labeled opioids to known processes such as flow cytometry. Attempts to utilize the reagent of Formula I in flow cytometry can be hampered by the extremely small particle size of the particles bearing opioid receptor sites, resulting in difficulty in obtaining an indication of the presence of such sites through observation of fluorescence of the bound reagent. By use of the dual biological functionality of the reagent of Formula III, the target particles may aggregate on both sides of the reagent, thereby enhancing the fluorescence and facilitating the detection and quantification of receptor sites.

In preparation of the reagent of Formula III, 3,6-diaminoacridine, or a hydrohalide thereof, is reacted with two molecules of an opioid ketone, such as, for example, oxycodone or oxymorphone, preferably in the presence of a Lewis acid catalyst such as zinc chloride. As in the preparation of the reagents of Formula I, reaction is preferably carried out in a liquid medium comprising both a solvent for the reactants, such a tetrahydrofuran, and a non-solvent for the product such as, for example, a primary alcohol. The product is recovered by crystallization.

Preparation of the compounds of formula IA $$Fl=N-N=R \qquad (IA)$$

can be carried out in essentially the same manner as the preparation of the fluorescent compounds of formula III, but no Lewis acid catalyst is required. To carry out the reaction, an opiate hydrazone is mixed with a fluorescent compound containing an active keto group, and reaction carried out either acatalytically or in the presence of a mineral acid such as HCl.

In accordance with the method of the invention, a fluorescent reagent of the invention is used for the detection and/or quantification of opioid sites in a sample of tissue, cells, or subcellular particles. In this method, the cells are contacted in vivo with the fluorescent reagent in a suitable medium which comprises a solvent for the reagent, for example, a mixture of ethyl alcohol and water buffered to approximately the pH of the physiological environment to which the sample cells or tissues are ordinarily exposed in vivo. The mixture of sample and reagent is incubated, preferably at about 37° C., to promote binding of the reagent to any receptor sites on the sample substrate. After incubation, the sample is washed for removal of excess reagent, and then observed for fluorescence, the presence of which indicates that the reagent has been bound to opioid receptor sites in the sample. Quantification of the number and/or distribution of receptor sites may be established by quantitative measurement of the fluorescent emission from the sample after removal of unbound fluorescent reagent. For example, the receptor sites may be quantified by measuring the intensity of fluorescence as compared to the intensity observed with a standard sample having a known concentration or distribution of receptor sites, and which has been incubated in the same manner with the same fluorescent reagent composition.

Alternatively, the extent of binding of the fluorescent reagent may be evaluated by the fluorescence polarization technique described by Dandliker et al., "Investigation of Hormone-Receptor Interactions by Means of Fluorescence Labeling," *Cancer Research,* Vol. 38, pp. 4214–4224, November 1978. In this method, reaction between the labeled opioid and the binding site results in an increase in the size of the microscopic unit bearing the fluorescer, thus retarding rotary brownian motion in a liquid vehicle. As a consequence, the fluorescent emission from the sample tends to be concentrated in a particular plane, and thus polarization increases as a function of the extent of binding, i.e., with the concentration of binding sites. If the concentration of binding sites is low, the relatively small labeled opioid molecules rotate more freely in the medium, resulting in relatively less polarization. Thus, fluorescence polarization can be conducted without the necessity of any separation step such as adsorption or sedimentation. Only simple optical measurement is required to obtain the ratio of bound to free labeled opioid. Fluorescence polarization is particularly advantageous for use in conjunction with dilution jump techniques for discriminating between binding sites of high and low affinity for the opioid through observation of the reverse dissociation reaction. See the aforesaid Dandliker article which is expressly incorporated herein by reference.

Using these basic techniques, the present invention provides a method for determining the distribution of opioid receptors in a tissue sample, and an in vitro analysis for detecting a neurological disorder, addiction, tolerance or other pathological condition of a patient. In these in vitro procedures, a tissue sample is stained by contacting it with a fluorescent reagent in the manner generally described above, and the staining pattern obtained is observed and compared with the staining pattern obtained upon contacting a standard tissue specimen with the reagent. In this manner, the distribution of receptor sites in the sample can be determined, a histochemical characteristic of the sample can be determined where the specimen has a known histochemical characteristic, and an addiction, tolerance, neurological disorder or other pathological condition in the patient may be determined where the source of the standard specimen is associated with any such conditions. Preferably, the staining pattern obtained with the unknown sample is compared with the staining patterns of a set or library of known staining patterns, each pattern of the library being associated with a known histochemical characteristics, known neurological disorder, etc., use of a library of specimens allows a more complete and definitive determination of the characteristics of the unknown sample.

Comparative analysis may also be conducted by competitive binding assays. Unknown levels of binding sites can be determined by incubating a sample with specified known concentrations of fluorescent labeled reagent and non-fluorescent labeled opioid, and comparing the resulting emission intensity or fluorescence polarization with that observed upon incubating various known concentrations of receptors with the same concentrations of fluorescent and non-fluorescent opioids. Because the fluorescent labeled opioid typically has quantitative binding characteristics an order of magnitude below those of the unlabeled opioid, the non-fluorescent labeled reagent used in the assay may advantageously have a moiety substituted at the 3-position to provide modified binding characteristics at a level comparable to that of the fluorescent reagent.

Use of the method of invention for in vitro determination of a neurological disorder, addiction or other pathological disorder normally requires a biopsy of suspected tissue, a procedure that may not be applicable to all clinical situations, particularly where brain tissue is involved. Although there are receptor sites for opioids in organs of the body other than the brain thereby rendering the in vitro analysis of a biopsy sample a viable approach in at least certain instances, it has further been discovered that the fluorescent reagents of the invention may be radiolabeled and used in a novel in vivo method for determining neurological disorders, etc., in the brain or other target organ in the patient.

The reagent used in the in vivo method of the invention is preferably radiolabeled by use of a fluorescer containing a radioactive isotope. For example, the fluorescent moiety of the reagent may be a di-131-iodofluoresceinyl group, or one or more carbons or nitrogens of the fluoroescer may be a radioactive isotope, such as carbon-14 or nitrogen-15.

In carrying out the in vivo method of the invention, the radiolabeled fluorescent reagent, in a pharmaceutically acceptable carrier such as a buffered alcohol/water mixture, is injected into the patient's body. After a quantity of the reagent has become bound to receptor sites of the target organ, the radioactive emission pattern in the region of the organ is observed. This emission pattern is compared with a standard binding pattern of the fluorescent reagent that is associated with a known neurological disorder, addiction, tolerance or other pathological condition. Such standard pattern may, for example, be the fluorescent staining pattern obtained by contacting a standard organ tissue specimen in vitro with the fluorescent reagent. In this instance the standard specimen is from an organ afflicted with a known condition or disorder. Alternatively, the standard pattern may be a radioactive emission pattern obtained after injecting the radiolabeled fluorescent reagent into a patient afflicated with a known disorder or condition. In either instance, the unknown emission pattern from the target organ is preferably compared with a set or library of standard patterns in order to facilitate complete and accurate diagnosis.

Use of the fluorescent-labeled reagent is particularly advantageous where the standard binding patterns are provided by in vitro observation of fluorescent staining. In obtaining the in vivo binding pattern, it is preferable to use the same (or a radiolabeled derivative of the same) fluorescent reagent used to obtain staining patterns for the standard specimens. Thus, the reagent injected into the patient provides the same binding characteristics as have been involved in obtaining the standard specimen staining patterns. As noted above, binding characteristics are altered, the binding affinity generally lowered, by attachment of the fluorescer to the opioid.

The following examples illustrate the invention.

EXAMPLE 1

Synthesis of 1-(N)-Fluoresceinyl Naloxone Thiosemicarbazone ("6-FN")

Naloxone hydrazone (0.114 grams; 0.333 millimoles) was added to a solution of fluorescein isothiocyanate (0.1351 gram; 0.347 millimoles; Sigma Chemical, St. Louis, isomer I) in tetrahydrofuran (2 ml.; Fisher Certified) and ethyl alcohol (4 ml.; 100%, histological quality). The resulting solution was stirred at room temperature until the reaction mixture contained no more naloxone hydrazone as indicated by a thin layer chromatography (TLC). The container was wrapped in aluminium foil. Thereafter, portions of ethyl alcohol and water were added to the reaction mixture. Orange crystals formed which were filtered off and dried. The structure of the crystals was determined to be that of 1-(N)-fluoresceinyl naloxone thiosemicarbazone ("6-FN") based on spectroscopic evidence and elemental analysis. Major physical and spectral characteristics of 6-FN included: Mp 300°. IR (nujol): $\nu$1740 (C=C), 1635, 1590, 1500, 1325, 1268, 1208, 1182, 1110, 1028, 993, 952, 912, 852, 808, 722, 618 cm$^{-1}$. $^1$H-NMR (100 MHz) (DMSO-d$_6$): $\delta$8.442 (1H, d, J~2 Hz), $\delta$8.034 (1H, split d, J~8 Hz, J~2 Hz), 7.251 (1H, d, J~8 Hz) (protons from the non-phenolic aromatic ring of the fluorescein moiety); 6.678, 6.602, 6.583 (8H's, single peaks) (aromatic protons from the phenol rings of the fluorescein and naloxone moieties); 6.11–5.10 (complex signal, vinylic H's of the allyl group); 5.029 (1H, s, bridgehead H at C—5) ppm; the upfield peaks look like those of naloxone. C, H, N, S analysis: calculated: C, 65.74; H, 4.69; N, 7.67; S, 4.39. Found: C, 65.81; H, 4.64; N, 7.64; S, 4.34. Fluorescence properties of 6-FN: (a) A $10^{-6}$M solution in pH 7 phosphate buffer showed an excitation maximum at 493 nm and an emission maximum at 513 nm, as compared to 493 nm and 510–511 nm, respectively, for free fluorescein; (b) Absorption maximum $10^{-5}$M solution (phosphate buffer) was at 493 nm (A=0.410; (c) Quantum yield of 6 FN compared to free fluorescein was about 67% at $10^{-9}$M; d) fluorescence polarization was 0.038 for 6-FN and 0.022 for free fluorescein.

EXAMPLE 2

Preparation of 1-(N)-tetramethylrhodaminyl-B-naloxone Thiosemicarbazone ("6RN")

Tetramethylrhodaminyl-B-isothiocyanate (Sigma, St. Louis; 10 mg.; 2.255×10-5 moles) was almost completely dissolved in a mixture of tetrahydrofuran and ethyl alcohol (approximately 3 cc), producing a wine-red solution. To this solution was added naloxazone, i.e., naloxone hydrazone, (8.5 mg.; 2.49×10-5 moles). After the naloxazone was added, the solution changed from wine-red to a brownish color and became cloudy. After 33 minutes of reaction, a sample of the reaction solution was removed and subjected to thin-layer chromatographic analysis. The results of this analysis did not indicate the presence of any remaining naloxazone. Approximately one half hour after the addition of naloxazone, the reaction mixture was quenched by addition of water. Upon quenching, the solution warmed slightly, but no precipitate formed. Thereafter, the solution was concentrated to approximately its initial volume by removal of solvent on a rotary evaporator until mild heating. Significant foaming was observed during the concentration of the solution, and a precipitate formed which was separated by filtration. Thereafter, the mother liquor was subjected to further evaporation to one quarter of the original volume, upon which additional precipitation occurred, producing a second crop of crystals which was also removed by filtration. Both crops of crystals were dried in a vacuum oven. The product was 1-(N)-tetramethylrhodaminyl-B-naloxone thiosemicarbazone.

EXAMPLE 3

Synthesis of 1-(N)-Fluorosceinyl Naltrexone Thiosemicarbazone ("6-FNX")

Naltrexazone (0.0573 grams; 1.61×$10^{-4}$ moles) was dissolved in a minumum amount of tetrahydrofuran and the resulting solution added (together with ethyl alcohol rinsings from the container in which the dissolution was carried out) to a stirred solution of fluorescienyl isothiocyanate (Sigma Chemical, Isomer I; 0.0641 grams; 1.65×$10^{-4}$ mol.) in THF (1 cc; Fisher, certified) and ethyl alcohol (2 cc). As soon as the naltrexazone was added, the color of the fluorescienyl isothiocynate solution began changing from red to orange. Reaction was carried out under agitation at room temperature while the reaction solution was protected from light with aluminum foil. After approximately one hour and 5 minutes of reaction, a small quantity of precipitate was formed and a sample taken for TLC analysis. Thereafter, additional ethyl alcohol was added until further precipitation was obtained. After one hour and 35 minutes the reaction was stopped by filtering out the solid precipitate. The solid product was washed twice with ethyl alcohol, yielding a crystallizate of 1-(N)-fluoresceinyl naltrexone thiosemicarbazone ("6-FNX") (0.0223 grams), determined by TLC analysis to be substantially pure.

Further crystallization from the mother liquor yielded an additional quantity of 6-FNX (0.0182 grams). By adding water to the remaining mother liquor, a third crop of crystalline 6-FNX was obtained (0.0410 grams). The third crop was washed with ethyl alcohol and water. Overall yield at this point was 67.9%. Further crystallization from the mother liquor provided a fourth crop of 6-FNX crystals (0.0138 grams) bringing the total yield to 79.4%.

EXAMPLE 4

Synthesis of 1-(N)-Fluoresceinyl Oxymorphone thiosemicarbazone ("6-FO").

Oxymorphazone (0.1072 grams; 0.3403 millimoles) was added to a solution of fluorescein isothiocyanate (Sigma, Isomer 1; 0.1419 grams; 0.3644 millimoles) dissolved in ethyl alcohol (4 cc; 100%) and tetrahydrofuran (2 cc; Fisher, certified). As soon as the oxymorphazone was added, the color of the fluoresceinyl isothiocyanate solution changed from red to orange. Reaction was carried out under agitation at room temperature for 3 hours and 45 minutes, during which the reaction mixture was protected from light with aluminum foil.

Immediately upon mixing of the reactants, an orange precipitate began forming. After three hours of reaction a substantial amount of precipitate had formed, and ethyl alcohol (2 cc) was added to the reaction mixture. Thereafter, a sample was taken for TLC analysis, the results of which indicated that no oxymorphazone was left in the reaction system. After the reaction was terminated, the product was separated by filtration and the red solid product was washed repetitively with water and ethyl alcohol.

Water was added to the mother liquor and an orange precipitate formed which was separated by filtration and also washed repetitively with water and ethyl alcohol.

The first crop of crystals was a red solid (0.0851 g), and the second crop an orange solid (0.0353 g). After the mother liquor from the second crystallization was allowed to stand, further quantities of red precipitate formed, and this precipitate was separated by filtration (0.0409 g). Thus, the overall yield was 67.3%.

TLC analysis in the 4:1:0.5 chloroform/ethyl alcohol/dimethylformamide system established that all four crops of crystals were consistent with 6-FO. A portion (0.0192 grams) of first crop crystals was subjected to elemental analysis with the following results:

|  | Calculated | Found |
| --- | --- | --- |
| carbon | 64.76% | 62.35% |
| hydrogen | 4.58% | 4.98% |
| nitrogen | 7.95% | 7.23% |
| sulfur | 4.55% | 4.15% |
| oxygen | 18.16% | — |
| Total: | 100% |  |

The sample submitted for elemental analysis was very hygroscopic. Repeated C—H analysis after additional drying indicated a carbon content of 62.71% and a hydrogen content of 4.88%.

EXAMPLE 5

1-(N)-fluoresceinyl benzophenone thiosemicarbazone ("6-FB") was synthesized in a manner comparable to the methods described in Examples 1-4.

The opioid receptor binding characteristics of 6-FN, 6FNX, 6-FO, 6-FB, and 6-RN were assessed by their effectiveness in displacing dihydromorphine ($^3$H-DHM) from rat brain synaptosomal plasma membranes. In this assessment, radiolabeled $^3$H-DHM ($^3$H-DHM*) was initially bound to the receptor sites on the membranes, following which the membranes were contacted with solutions of the fluorescent-labeled reagent. After removal of the reagent solution, the membranes were washed for removal of any displaced $^3$H-DHM*. Radioactivity counting both before and after treatment with the fluorescent reagent gave an indication of displacement of $^3$H-DHM*.

All of the fluorescent-labeled compounds except 6-FB were found effective for displacement of $^3$H-DHM*. Increasing concentrations of the fluorescent reagents were effective for progressive displacement of the indicator ligand. Generally, the fluorescent reagents were not as effective as their parent opioids as competitors for displacement of $^3$H-DHM*. However, 6-FN, 6-FNX, 6-FO and 6-RN showed sufficient binding activity for use in the detection and quantification of receptor sites in the synaptosomal membranes. The following IC$_{50}$ values (concentrations necessary for 50% displacement of $^3$H-DHM*) were determined graphically: naloxone 0.9 nM; 6-FN 20 nM, 6-RN 12 nM; naltrexone 0.3 nM; 6-FNX 5 nM; 6-FO 20 nM. The control compound 6-FB was inactive at $10^{-6}$M. The Hill coefficients were: naloxone 1.09; 6-FN 0.671; 6-RN 1.09; naltrexone 1.15; 6-FNX 0.675; 6-FO 0.989.

In order to investigate the anomalous displacement curve of 6-FN, this reagent was also subjected to the site selectivity analysis technique described by Terenius and Wahlström, *European Journal of Pharmacology*, Vol. 40, pp. 241-248 (1976). In this anslysis, $^3$H-DHM and H-D-Ala$^2$-[Leu]enkephalin ($^3$H-DALE) were used as indicator ligands. To provide a comparison of site selectivity, the non-peptide antagonist compound was tested for displacement of labeled opioid from a substrate which had been previously contacted with an indicator ligand solution containing DHM* (0.43 nM) and cold DALE (0.43 nM). These results were compared with the displacement obtained from a substrate which had been contacted with an indicator ligand solution containing cold DHM (0.43 nM) and DALE* (0.43 nM). FIG. 1 is a plot of percent bound DALE* as obtained from the second displacement test versus percent bound DHM* from the first displacement test for a series of antagonist compound solutions of varying strength. In FIG. 1 it will be noted that compounds which displace the two indicator ligands differently provide a curve which is convex towards the axis of the labeled indicator ligand which is less favorably displaced. The results of this test show clearly the difference between 6-FN and naloxone with respect to site selectivity. The IC50 values determined graphically from this test were here: (a) with $^3$H-DHM; naloxone 1.3 nM; 6-FN 12 nM; (b) with $^3$H-DALE; naloxone 20 nM; 6-FN 17 nM.

EXAMPLE 6

6-FN was tested for activity on an electrically stimulated guinea pig ileum longitudinal muscle preparation. In this test, a specimen of guinea pig ileum was stretched between two wires in a nutrient solution (2.5 mil.) and stimulated supramaximally at 0.1 Hz. In the absence of opioid agonists and antagonists electrical stimulation of the muscle results in contraction.

Figure 2:
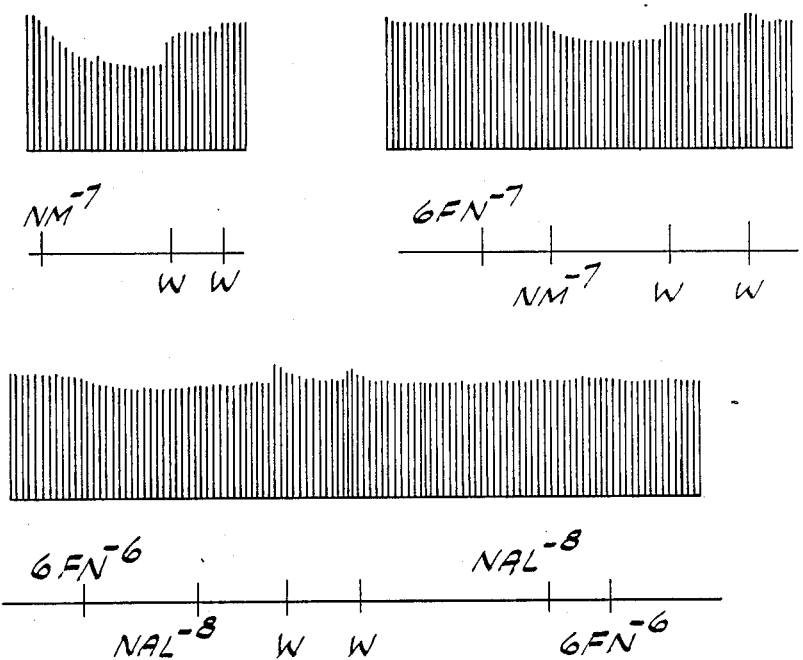
FIG. 2 illustrates the agonist effect of normorphine in inhibiting the contraction of guinea pig ileum; the antagonist effect of 6-FN with respect to normorphine; the slight agonist effect of 6-FN; and the antagonist effect of naloxone with respect to 6-FN.

Addition of an aqueous solution of normorphine (25 microliters; $10^{-7}$M) substantially inhibited contraction of the muscle (FIG. 2). Introduction of an aqueous solution of 6-FN ($10^{-6}$M in 10% ethanol; 25 microliters) into the nutrient solution (final 6-FN concentration: $10^{-7}$M) prior to the introduction of normorphine significantly inhibited the agonist effect of normorphine; though the effect was ten times less effective than the inhibiting effect achieved with naloxone. Washing of the ileum specimen did not readily eliminate the antagonist effect. In this respect 6-FN was similar to naloxone.

As illustrated in FIG. 2, $10^{-6}$M 6-FN exhibited a partial agonist activity which was observed to be reversible with $10^{-7}$M naloxone.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A fluorescent reagent useful as a receptor probe in the detection and quantification of tissue, cells, and subcellular particles containing opioid receptors, said reagent corresponding to the formula:

or

where Fl is a fluorescent moiety that emits visible light at a frequency different from any frequency at which light is emitted by any fluorescent moiety endogenous to human brain tissue, and R is a nonpeptide opioid moiety having a morphine or morphinan structure.

2. A fluorescent reagent as set forth in claim 1 wherein R corresponds to the formula:

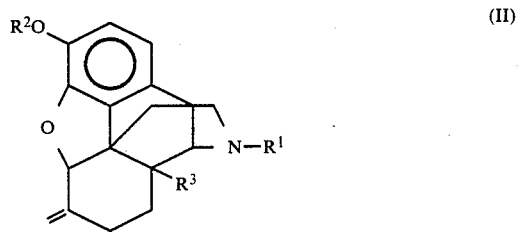

where $R^1$ is selected from the group consisting of hydrogen, alkyl, alkenyl and alicyclic substituents, $R^2$ is selected from the group consisting of hydrogen, alkyl and acyl, and $R^3$ is selected from the group consisting of hydrogen, hydroxyl and acyloxy.

3. A fluorescent reagent as set forth in claim 2 wherein the linking group between said fluorescent moiety and said opioid moiety is

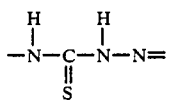
(IX)

Fl is selected from the group consisting of substituted and unsubstituted fluoresceinyl and rhodaminyl.

4. A fluorescent reagent as set forth in claim 3 wherein Fl is fluoresceinyl.

5. A fluorescent reagent as set forth in claim 4 wherein $R^1$ is cyclopropylmethyl, $R^2$ is hydrogen, and $R^3$ is hydroxyl.

6. A fluorescent reagent as set forth in claim 4 wherein $R^1$ is methyl, $R^2$ is hydrogen, and $R^3$ is hydroxyl.

7. A fluorescent reagent as set forth in claim 4 wherein $R^1$ is 2-propenyl, $R^2$ is hydrogen and $R^3$ is hydroxyl.

8. A fluorescent reagent as set forth in claim 3 wherein Fl is di-131-iodofluoresceinyl.

9. A fluorescent reagent as set forth in claim 3 wherein Fl is tetramethylrhodaminyl-B-.

10. A fluorescent reagent as set forth in claim 9 wherein $R^1$ is 2-propenyl, $R^2$ is hydrogen, and $R^3$ is hydroxyl.

11. A fluorescent reagent useful as a receptor probe in the detection and quantification of tissue, cells, and subcellular particles containing opioid receptors, said reagent corresponding to the formula:

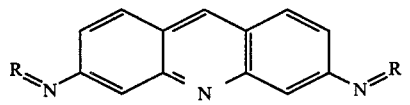
(III)

where R is a nonpeptide opioid moiety having a morphine or morphinan structure.

12. A fluorescent reagent as set forth in claim 11 wherein R corresponds to the formula

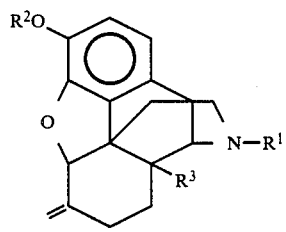
(II)

where $R^1$ is selected from the group consisting of hydrogen, alkyl, alkenyl, and alicyclic substituents, $R^2$ is selected from the group consisting of hydrogen, alkyl, and acyl, and $R^3$ is selected from a group consisting of hydrogen, hydroxyl and acyloxy.

13. A fluorescent reagent as set forth in claim 12 wherein $R^1$ is 2-propenyl, $R^2$ is hydrogen, and $R^3$ is hydroxyl.

14. A fluorescent reagent as set forth in claim 12 wherein $R^1$ is methyl, $R^2$ is hydrogen, and $R^3$ is hydroxyl.

15. A fluorescent reagent as set forth in claim 12 wherein $R^1$ is cyclopropylmethyl, $R^2$ is hydrogen, and $R^3$ is hydroxyl.

16. A method for detecting opioid receptors in a sample of tissue, cells, or subcellur particles, comprising the steps of:
contacting said sample with a receptor probe reagent selected from the group consisting of fluorescent reagents corresponding to the formulae

(I)

(IA)

and

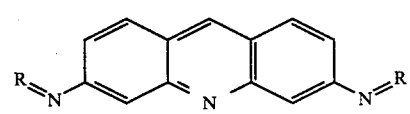
(III)

where Fl is a fluorescent moiety which emits visible light at a frequency different from any frequency at which visible light is emitted by any component endogenous to human brain tissue, and R is a non-peptide opioid moiety having a morphine or morphinan structure;
removing unbound fluorescent reagent from said sample; and
thereafter observing the sample for fluorescence inidicating bonding of said reagent to receptor sites in said sample.

17. A method as set forth in claim 16 wherein the receptor sites in said sample are quantified by quantitative measurement of the fluorescent emission from said sample after removal of unbound fluorescent reagent.

18. A method for determining the distribution of a particular type of opioid receptor site in a tissue sample, comprising the steps of:
contacting said sample with a receptor probe reagent selected from the group corresponding to the formulae:

(I)

(IA)

and

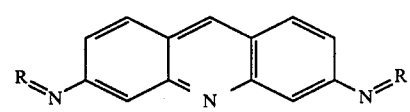
(III)

wherein Fl is a fluorescent moiety which emits visible light at a frequency different from any frequency at which visible light is emitted by any component endogenous to human brain tissue, and R is a non-peptide opioid moiety having a morphine or morphinan structure; and
observing the fluorescent staining pattern exhibited by said sample after contacting said sample with said reagent, thereby providing an indication of said distribution.

19. A method as set forth in claim 18 wherein, in formulae I, IA and III, R corresponds to the formula

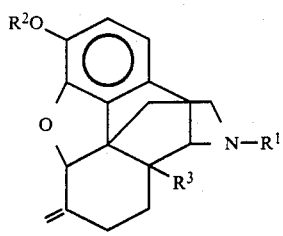

(II)

wherein $R^1$ is selected from a group consisting of hydrogen, alkyl, alkenyl, and alicyclic, $R^2$ is selected from the group consisting of hydrogen, alkyl, and acyl, and $R^3$ is selected from a group consisting of hydrogen, hydroxyl and acyloxy.

20. A method as set forth in claim 19 wherein said fluorescent reagent corresponds to formula I or IA.

21. A method as set forth in claim 20 where the linking group between said fluorescent moiety and said opioid moiety is

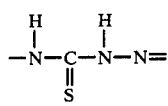

(IX)

and Fl is selected from a group consisting of substituted and unsubstituted fluoresceinyl and rhodaminyl.

22. A method as set forth in claim 21 wherein Fl is fluoresceinyl, $R^1$ is cyclopropylmethyl, $R^2$ is hydrogen, and $R^3$ is hydroxyl.

23. A method as set forth in claim 21 wherein Fl is fluoresceinyl, $R^1$ is methyl, $R^2$ is hydrogen, and $R^3$ is hydroxyl.

24. A method as set forth in claim 21 wherein Fl is fluoresceinyl, $R^1$ is 2-propenyl, $R^2$ is hydrogen, and $R^3$ is hydroxyl.

25. A method as set forth in claim 21 wherein Fl is tetramethylrhodaminyl-B-, $R^1$ is 2-propenyl, $R^2$ is hydrogen and $R^3$ is hydroxyl.

26. A method as set forth in claim 18 wherein said staining pattern is compared with the staining pattern obtained upon contacting a standard tissue specimen with said reagent, said standard specimen having a staining pattern associated with a known histochemical characteristic, thereby determining a histochemical characteristic of said sample.

27. A method as set forth in claim 26 wherein said staining pattern of said sample is compared with staining patterns of a set of known staining patterns, each pattern of said set being associated with a known histochemical characteristic, whereby a histochemical characteristics of said sample is determined.

28. A method for detecting a neurological disorder, addiction, tolerance or pathological condition of a patient by in vitro analysis of a tissue sample taken from an organ of said patient, the method comprising contacting said sample with a receptor probe reagent selected from the group consisting of fluorescent reagents corresponding to the formulae

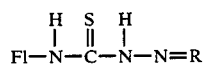

(I)

Fl=N—N=R    (IA)

and

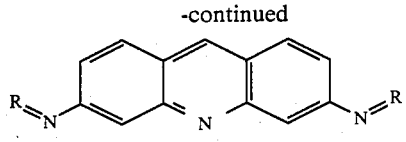

(III)

wherein Fl is a fluorescent moiety which emits visible light at a frequency different from any frequency at which visible light is emitted by any component endogenous to human brain tissue, and R is a nonpeptide opioid moiety having a morphine or morphinan structure;

observing the fluorescent staining pattern exhibited by said sample after contacting said sample with said reagent; and comparing said staining pattern with the staining pattern obtained upon contacting a standard tissue specimen with said reagent, said standard specimen having a staining pattern associated with a known neurological disorder, addiction, tolerance, or other pathological condition.

29. A method as set forth in claim 28 wherein, in formulae I, IA and III, R corresponds to the formula

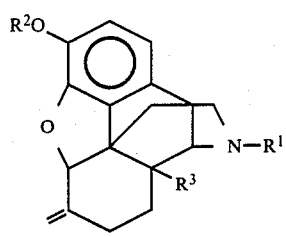

(II)

wherein $R^1$ is selected from a group consisting of hydrogen, alkyl, alkenyl, and alicyclic, $R^2$ is selected from the group consisting of hydrogen, alkyl, and acyl, and $R^3$ is selected from a group consisting of hydrogen, hydroxyl and acyloxy.

30. A method as set forth in claim 29 wherein said fluorescent reagent corresponds to formula I or IA.

31. A method as set forth in claim 30 where the linking group between said fluorescent moiety and said opioid moiety is

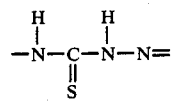

(IX)

and Fl is selected from a group consisting of substituted and unsubstituted fluoresceinyl and rhodaminyl.

32. A method as set forth in claim 31 wherein Fl is fluoresceinyl, $R^1$ is cyclopropylmethyl, $R^2$ is hydrogen, and $R^3$ is hydroxyl.

33. A method as set forth in claim 31 wherein Fl is fluoresceinyl, $R^1$ is methyl, $R^2$ is hydrogen, and $R^3$ is hydroxyl.

34. A method as set forth in claim 31 wherein Fl is fluoresceinyl, $R^1$ is 2-propenyl, $R^2$ is hydrogen, and $R^3$ is hydroxyl.

35. A method as set forth in claim 31 wherein Fl is tetramethylrhodaminyl-B-, $R^1$ is 2-propenyl, $R^2$ is hydrogen, and $R^3$ is hydroxyl.

36. A method as set forth in claim 28 wherein said staining pattern of said sample is compared with staining patterns of a set of known staining patterns, each pattern of said set being associated with a known neurological disorder, addiction, tolerance or other pathological condition.

* * * * *